US012759988B2

(12) United States Patent
Zhu et al.

(10) Patent No.: US 12,759,988 B2
(45) Date of Patent: Oct. 13, 2026

(54) COMPOUND FOR TREATING DISEASES RELATED TO CEREBRAL ISCHEMIC INJURY

(71) Applicant: JIANGSU CHIA TAI FENGHAI PHARMACEUTICAL CO., LTD., Yancheng (CN)

(72) Inventors: Yongqiang Zhu, Yancheng (CN); Jia Liu, Yancheng (CN); Jia Wang, Yancheng (CN); Qi Chen, Yancheng (CN); Yang Yang, Yancheng (CN)

(73) Assignee: JIANGSU CHIA TAI FENGHAI PHARMACEUTICAL CO., LTD., Yangcheng (CN)

( * ) Notice: Subject to any disclaimer, the term of this patent is extended or adjusted under 35 U.S.C. 154(b) by 370 days.

(21) Appl. No.: 18/580,794

(22) PCT Filed: Jul. 20, 2022

(86) PCT No.: PCT/CN2022/106618
§ 371 (c)(1),
(2) Date: Jan. 19, 2024

(87) PCT Pub. No.: WO2023/001164
PCT Pub. Date: Jan. 26, 2023

(65) Prior Publication Data

US 2024/0360094 A1 Oct. 31, 2024

(30) Foreign Application Priority Data

Jul. 21, 2021 (CN) ......................... 202110829381.4

(51) Int. Cl.
*C07D 307/83* (2006.01)
*A61K 31/365* (2006.01)
*A61P 9/10* (2006.01)
*A61P 25/00* (2006.01)

(52) U.S. Cl.
CPC .......... *C07D 307/83* (2013.01); *A61K 31/365* (2013.01); *A61P 9/10* (2018.01); *A61P 25/00* (2018.01)

(58) Field of Classification Search
CPC ............................ C07D 307/83; A61K 31/365
See application file for complete search history.

(56) References Cited

U.S. PATENT DOCUMENTS

2014/0288027 A1 9/2014 Wang et al.

FOREIGN PATENT DOCUMENTS

| | | | |
|---|---|---|---|
| CN | 101029037 | A | 9/2007 |
| CN | 102260233 | A | 11/2011 |
| CN | 107501250 | A | 12/2017 |
| WO | 2018/014834 | A1 | 1/2018 |

OTHER PUBLICATIONS

Qi et al, Novel Asymmetric organocatalytic Michael-aldol-dehydration domino reaction for the construction of spirocyclic benzofuranones, 2013, Tetrahedron, vol. 69, p. 9303-9308. (Year: 2013).*

Oct. 21, 2022 International Search Report issued in International Patent Application No. PCT/CN2022/106618.

Shen et al., "Improved Synthesis of 2-Butyl-5-Nitrobenzofuran", Guangdong Chemical Industry, vol. 40, No. 248, Jun. 30, 2013, pp. 6-7.

* cited by examiner

*Primary Examiner* — Adam C Milligan
*Assistant Examiner* — Karen Cheng
(74) *Attorney, Agent, or Firm* — Oliff PLC

(57) ABSTRACT

A compound for treating diseases related to cerebral ischemic injury. The structure of the compound is as represented by formula (II) below. The compound exhibits higher bioavailability and higher distribution concentrations in rat plasma and brain tissues, and shows a good efficacy in the treatment of ischemic brain injury.

(II)

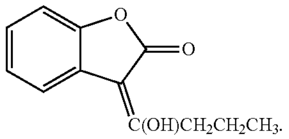

13 Claims, 1 Drawing Sheet

COMPOUND FOR TREATING DISEASES RELATED TO CEREBRAL ISCHEMIC INJURY

TECHNICAL FIELD

The present invention relates to compounds and pharmaceutical compositions that have anti-cerebral ischemia, anti-post-ischemic inflammation, and anti-convulsion effects and are capable of ameliorating neurological functional deficits in patients with ischemic cerebral stroke and a method for treating diseases related to ischemic cerebral neuronal injury and necrosis.

BACKGROUND ART

White matter is an important component of the central nervous system and is a place where nerve fibers aggregate. White matter lesions (WML) are usually caused by reduced blood flow and insufficient oxygen supply to the blood vessels. In the presence of dysfunction (insufficiency) in the blood supply to the brain, a series of symptoms ensue due to the difficulty in meeting the metabolic needs of brain tissues. The clinical manifestations may include dizziness, headache, numbness of limbs, or transient loss of consciousness, and for serious cases, there may be irreversible damage to brain function and even death. Diseases related to cerebral ischemia include transient ischemic attack (TIA), ischemic cerebral stroke (cerebral infarction), moyamoya disease, chronic cerebral circulatory insufficiency, and the like. These conditions are also contributing factors to the decline in cognitive function and vascular dementia in patients.

At present, there are numerous drugs for treating diseases caused by cerebral ischemia, but only a few are truly effective. Nimodipine, a currently available drug, has a preventive effect on cerebral ischemia, but the therapeutic efficacy is not certain. 3-n-butylphthalide (NBP), extracted from celery seed volatile oil, was approved in China in 2005 to be used for treating mild to moderate acute ischemic cerebral stroke, but the action mechanism is not clear at present, and clinical use can lead to adverse reactions such as abnormal liver function, digestive tract reaction, and the like.

Cerebral ischemia may cause cerebral nerve injury and necrosis in different degrees and thereby result in corresponding system dysfunction of the human body, greatly reducing the life quality of patients. There is still a need to provide other compounds exhibiting superior efficacy, possessing anti-cerebral ischemia, anti-post-ischemic inflammation, and anti-convulsion effects, and are capable of ameliorating neurological functional deficits in patients with ischemic cerebral stroke, alleviating dysmnesia, and protecting nerve cells and blood brain barrier, and the like.

SUMMARY

The present invention provides a novel compound that has anti-cerebral ischemia, anti-post-ischemic inflammation and anti-convulsion effects and is capable of ameliorating neurological functional deficits in patients with ischemic cerebral stroke, and the compound is used for treating diseases related to ischemic cerebral neuronal injury and necrosis.

The present invention provides a compound of formula (II) or a pharmaceutically acceptable salt thereof:

(II)

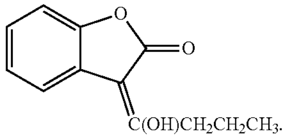

The present invention further provides a compound of formula (I) or a pharmaceutically acceptable salt thereof:

(I)

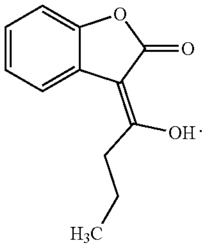

The present invention also provides a pharmaceutical composition, which comprises the compound of formula (II) or the pharmaceutically acceptable salt thereof described herein and one or more pharmaceutically acceptable carriers.

The present invention also provides a pharmaceutical composition, which comprises the compound of formula (I) or the pharmaceutically acceptable salt thereof described herein and one or more pharmaceutically acceptable carriers.

The present invention also provides use of the compound of formula (II) or the pharmaceutically acceptable salt thereof described herein in preparing a medicament for treating and/or preventing is diseases related to cerebral ischemic injury.

The present invention also provides use of the compound of formula (I) or the pharmaceutically acceptable salt thereof described herein in preparing a medicament for treating and/or preventing diseases related to cerebral ischemic injury.

The present invention also provides use of the composition described herein in preparing a medicament for treating and/or preventing diseases related to cerebral ischemic injury.

The diseases related to cerebral ischemic injury described herein include but are not limited to ischemic cerebral stroke, vascular dementia, post-ischemic inflammation, convulsion, ischemic neuronal injury or necrosis, and the like.

The present invention also provides a method for synthesizing the compound of formula (II) and the compound of formula (I) described herein.

In a specific example, the present invention also provides a method for preparing the compound of formula (I),

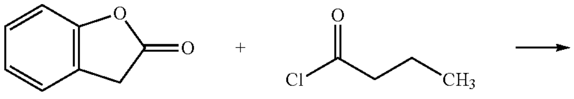

-continued

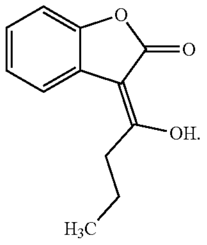

(I)

The present invention also provides a single crystal of the compound of formula (I) described herein, which has the following unit cell parameters:

| Crystal system | Monoclinic |
|---|---|
| Space group | $P2_1/c$ |
| a/Å | 7.318 (6) |
| b/Å | 20.279 (17) |
| c/Å | 7.458 (7) |
| α/° | 90 |
| β/° | 111.417 (16) |
| γ/° | 90 |
| Unit cell volume/Å3 | 1030.2 (16) |
| Z | 4 |

In a specific example, an asymmetric unit of the single crystal of the compound of formula (I) is shown in FIG. 2.

The present invention also provides a method for preparing the single crystal, which comprises: dissolving the compound of formula (I) described herein in petroleum ether, filtering, covering filtrate with a pinhole wrap, and placing the filtrate in a ventilated environment to allow a solvent to slowly evaporate at room temperature, thus obtaining the single crystal.

The compound described herein has higher bioavailability and higher distribution concentration in rat plasma and brain tissues and exhibits good efficacy on cerebral ischemic injury.

DETAILED DESCRIPTION

Figure 1:
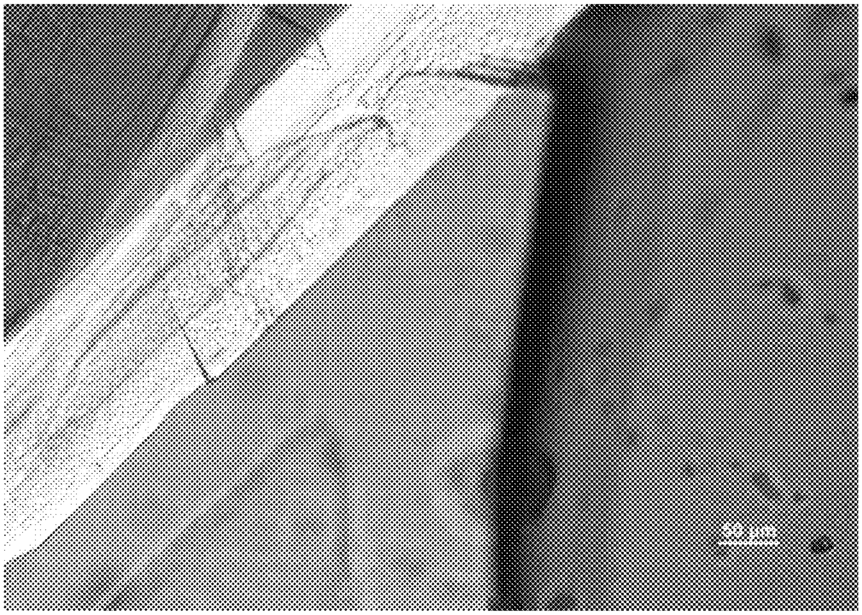
FIG. 1 is a micrograph of the single crystal of (Z)-3-(1-hydroxybutylidene)benzofuran-2 (3H)-one.

The present invention is further described below with reference to specific examples according to the general technical knowledge and conventional practice in the art. The following examples are only some of the preferred examples of the present invention and should not be construed as limiting the present invention, and it is apparent to those skilled in the art that several modifications can be made without departing from the scope of the present invention and these modifications shall also fall within the protection scope of the present invention.

Example 1

Synthesis of (Z)-3-(1-hydroxybutylidene)benzofuran-2 (3H)-one

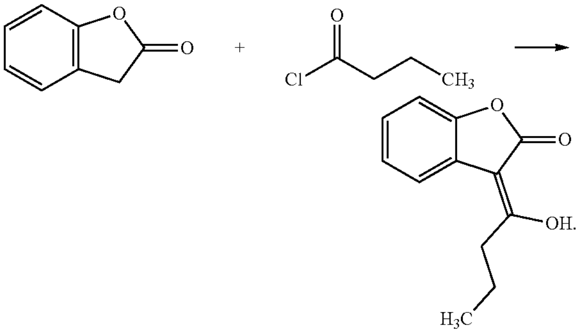

(I)

3-benzofuranone (5.0 g, 37.3 mmol, 1.0 eq.) was dissolved in dichloromethane (50 mL), and the mixture was cooled to 5° C., followed by addition of potassium tert-butoxide (6 g, 53.5 mmol, 1.4 eq.) slowly. The resulting mixture was reacted for 0.5 h, and then n-butyryl chloride (8 g, 75.0 mmol, 2.0 eq.) was added slowly. The mixture was reacted for 1 h, and water (50 mL) was added for extraction. The organic phase was washed with 0.1 N hydrochloric acid to be acidic (pH<2), dried over anhydrous sodium sulfate (5 g) for 0.5 h, filtered, and concentrated to give an oil product, which was then purified by high pressure preparative chromatography, and the purified solution was freeze-dried to give the compound of formula (I) (Z)-3-(1-hydroxybutylidene)benzofuran-2 (3H)-one (2.5 g, 32.9%) as a white solid.

$^1H$ NMR ($CDCl_3$, 400 MHz): δ12.02 (s, 1H), 7.35-7.33 (d, 1H), 7.28-7.17 (m, 3H), 2.76-2.73 (m, 2H), 1.90-1.80 (m, 2H), 1.12-1.08 (m, 3H).

$^1H$ NMR ($CDCl_3+D_2O$, 400 MHz): δ7.34-7.32 (d, 1H), 7.28-7.16 (m, 3H), 2.76-2.72 (m, 2H), 1.89-1.80 (m, 2H), 1.12-1.08 (m, 3H).

Example 2

Preparation of Single Crystal of (Z)-3-(1-hydroxybutylidene)benzofuran-2 (3H)-one 20 mg (0.098 mmol) of (Z)-3-(1-hydroxybutylidene)benzofuran-2 (3H)-one prepared in Example 3 was dissolved in petroleum ether (0.4 mL). The mixture was filtered, then the filtrate was covered with a pinhole membrane and placed in a fume hood, and the solvent was allowed to slowly evaporate at room temperature for 24 h to give the single crystal of (Z)-3-(1-hydroxybutylidene)benzofuran-2 (3H)-one (FIG. 1).

Figure 2:
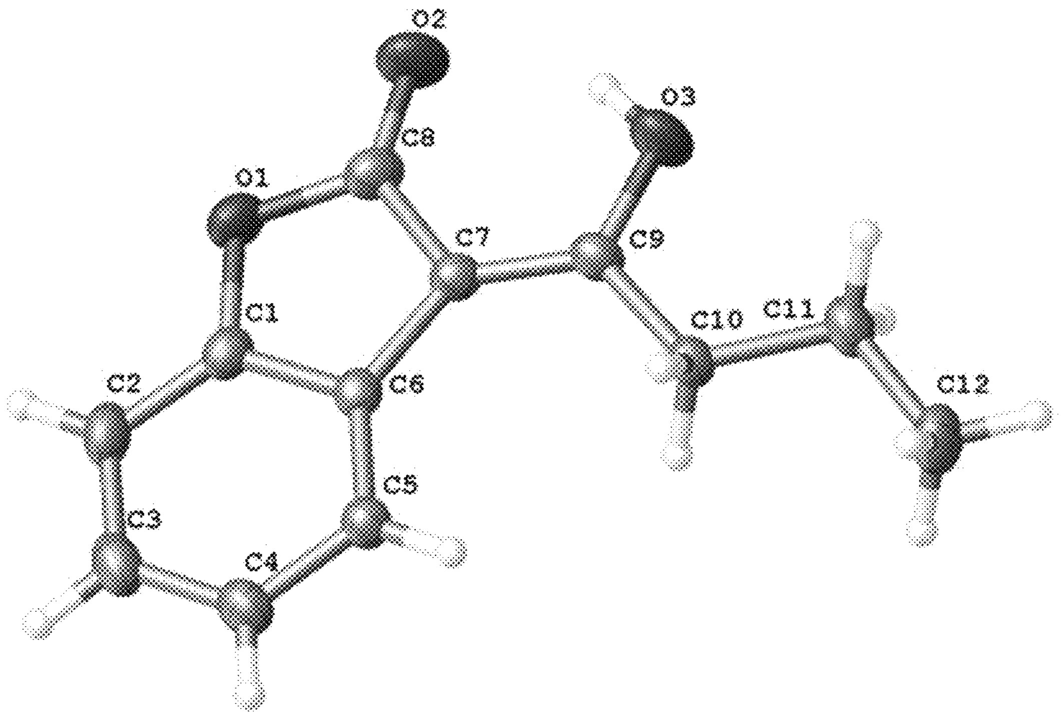
FIG. 2 is an asymmetric unit of the single crystal of (Z)-3-(1-hydroxybutylidene)benzofuran-2 (3H)-one.

The X-ray data of the single crystal of (Z)-3-(1-hydroxybutylidene)benzofuran-2 (3H)-one were collected on a Bruker D8 Venture diffractometer with the light source being Mo target Kα ray (λ=0.71073 Å). During data collection, the crystal was maintained at 296 K. Single crystal structure analysis was performed in Olex2 software. The Intrinsic Phasing method in the SHELXT program was used to calculate the initial structure and structure refinement was done by the least squares method of the SHELXL program. Crystallographic data and of structure refinement parameters (Z)-3-(1-hydroxybutylidene)benzofuran-2 (3H)-one are shown in Table 1, and asymmetric units of the single crystal of (Z)-3-(1-hydroxybutylidene)benzofuran-2-one are shown in FIG. 2.

TABLE 1

| Crystallographic data and structure refinement parameters of (Z)-3-(1-hydroxybutylidene)benzofuran-2(3H)-one | |
|---|---|
| Empirical formula | $C_{12}H_{12}O_3$ |
| Molecular weight | 204.22 |
| Temperature/K | 296.15 |
| Crystal system | Monoclinic |
| Space group | $P2_1/c$ |
| a/Å | 7.318 (6) |
| b/Å | 20.279 (17) |
| c/Å | 7.458 (7) |
| α/° | 90 |
| β/° | 111.417 (16) |
| γ/° | 90 |
| Unit cell volume/$Å^3$ | 1030.2 (16) |
| Z | 4 |
| $\rho_{calc}g/cm^3$ | 1.317 |
| $\mu/mm^{-1}$ | 0.094 |
| F(000) | 432.0 |
| Crystal size/$mm^3$ | 0.18 × 0.18 × 0.16 |
| Light source for diffraction | MoKα (λ = 0.71073 Å) |
| 2θ range for data collection/° | 4.018 to 54.558 |
| Diffraction index range | $-9 \le h \le 9$, $-25 \le k \le 26$, $-9 \le l \le 9$ |
| Number of collected diffraction points | 7840 |
| Number of independent diffraction points | 2303 [$R_{int}$ = 0.0291, $R_{sigma}$ = 0.0290] |
| Data/limit/parameter | 2303/0/138 |
| Goodness of fit based on $F^2$ | 1.057 |
| Final R factor [I ≥ 2σ (I)] | $R_1$ = 0.0511, $wR_2$ = 0.1280 |
| Final R factor [all data] | $R_1$ = 0.0662, $wR_2$ = 0.1389 |
| Peak/valley of maximum residual electron density/e $Å^{-3}$ | 0.23/−0.41 |

Biological Assays:

The following assays demonstrate that the compound (I) of the present invention can ameliorate ischemic neurological functional deficits. The assay results also show that the compound (I) of the present invention has good bioavailability and drug effect after oral administration.

Test 1: Pharmacokinetic Test in Rats

Male SD rats (weighing 180-260 g) were administered with compound (I) at a dose of 1.0 mg/kg by tail vein injection and at a dose of 10.0 mg/kg orally. Each group consisted of 3 animals. The solvent for administration was a solution of 5% DMSO+5% polyethoxylated castor oil (Cremophor EL) in normal saline. The rats were fasted for about 12 h before administration and were given ad libitum access to food 4 h after administration, and water was available all the time. Blood was collected from the orbit at about 0.2 mL before administration and 5 min, 15 min, 30 min, 1 h, 2 h, 4 h, 6 h, 8 h, and 24 h after administration. The samples were placed in EDTA-K2 anticoagulant EP tubes in an ice bath, and subjected to low-speed centrifugation at 4° C. and 3500 rpm for 10 min to isolate plasma, which was then stored at −20° C. before analysis. The concentration of compound (I) in the plasma was quantified by liquid chromatography-tandem mass spectrometry (LC-MS/MS). Pharmacokinetic parameters were calculated from the analysis results of the samples using WinNonlin software.

As can be seen from the data in Table 2, after oral administration, compared with the value reported in NBP-related literature (Wang Ningning, Li Yue, Li Xiaohong, Jiang Mingyan, RP-HPLC determination of the content of 3-n-butylphthalide in plasma of rats and pharmacokinetics thereof, Chinese Journal of New Drugs and Clinical Remedies, December 2012, Vol. 31, Issue 12, pp. 743-747), the compound (I) took longer to be cleared in rats and showed higher bioavailability (the bioavailability exceeding 100% is presumed to be caused by nonlinear pharmacokinetics).

TABLE 2

| Pharmacokinetic parameters | | | | | | |
|---|---|---|---|---|---|---|
| | | Compound (I) | | Butylphthalide (value in literature[1]) | | |
| Parameter | Unit | i.v. 1 mg/kg | p.o. 10 mg/kg | i.v. 10 mg/kg | p.o. 60 mg/kg |
| $T_{1/2}$ | h | 7.5 | 9.6 | 2.2 | 2.83 |
| $T_{max}$ | h | / | 0.5 | / | 0.7 |
| $C_{max}$ | ng/mL | / | 56533.3 | / | 2900.0 |
| $MRT_{inf}$ | h | 9.8 | 13.2 | 2.4 | 3.8 |
| $AUC_{0-t}$ | h*ng/ml | 52515.0 | 702610.0 | 7230.0 | 7110.0 |
| $AUC_{0-inf}$ | h*ng/ml | 59248.7 | 854122.3 | 8620.0 | 8560.0 |
| F | % | 144.2 | | 16.6* | |

*Calculated based on the literature value of $AUC_{0-inf}$ listed in the table

Test 2: Distribution in Brain Tissues of Rats

Male SD rats (weighing 200-270 g) were orally given compound (I) and butylphthalide (NBP) at a dose of 20 mg/kg separately. Plasma and brain tissue samples were collected from the animals at 0.5 h, 1 h, 4 h, and 24 h after administration. Collection of plasma: 0.2 mL of whole blood was collected by using an EP tube containing EDTA-K2 and centrifuged at 3500 g for 10 min, and then the upper plasma was collected and stored at −20° C. Collection of brain tissue: after the animals were euthanized, a proper amount of brain tissues were weighed out and homogenized with methanol in water (80%, w/v) at a ratio of 1:4. The concentration of compound in the plasma and brain tissue samples was quantified by liquid chromatography-tandem mass spectrometry (LC-MS/MS).

As can be seen from the data in Table 3, the distribution concentration of the compound (I) of the present invention in rat plasma and brain tissues was higher after oral administration.

TABLE 3

| Concentration of compound in rat plasma and brain tissues | | | | |
|---|---|---|---|---|
| | Compound (I) 20 mg/kg p.o. | | NBP 20 mg/kg p.o. | |
| Sampling time | Measured value in plasma Concentration (ng/ml) | Measured value in brain tissues Concentration (ng/g) | Measured value in plasma Concentration (ng/ml) | Measured value in brain tissues Concentration (ng/g) |
| 0.5 h | 241333.3 | 8733.3 | 26.0 | 28.5 |
| 1 h | 192333.3 | 5726.7 | 19.1 | 22.8 |
| 4 h | 182333.3 | 5030.0 | 7.2 | 10.2 |
| 24 h | 23500.0 | 285.3 | 1.7 | NA |

NA: below the lower limit of quantitation

Test 3: Pharmacodynamic Study of Compound in Rat Cerebral Stroke Model (Single Dose Administration)

Middle cerebral artery occlusion (MCAO) models of SD rats were constructed using the suture occlusion method to evaluate the protection effect of the compound on neurons of rats after cerebral ischemia-reperfusion. After anesthesia induction with 3.0% isoflurane in SD rats (240-270 g), the operation was performed, and the right-side neck area was dissected to reveal the right common carotid artery (CCA), external carotid artery (ECA) and internal carotid artery (ICA). The ECA was ligated. The ICA was temporarily occluded. Sutures were threaded at both the proximal end and the distal end of CCA. The distal end was securely ligated, and a loosely tied knot was placed at the proximal end. A small incision was made on the CCA between these two sutures. A No. 4-0 suture was inserted through the incision of CCA and slowly and gently pushed into the ICA. The threading was stopped temporarily when reaching the artery clamp of ICA. The pre-ligation suture was further tightened. The artery clamp blocking the blood flow in the ICA was removed, allowing the suture occlusion to be advanced into the ICA until it entered the intracranial region. When the suture was inserted about 18 mm away from the bifurcation of the CCA, slight resistance was felt, which shows the head end of the suture already entered the anterior cerebral artery (ACA), and the opening of the middle cerebral artery was already blocked by the side wall of the suture occlusion. The insertion was stopped at the moment, and the time was recorded. The artery clamp on the CCA was removed and the incision was closed after no active bleeding was observed. The ischemic rats were placed at room temperature to keep their body temperature at 37° C., and anesthesia induction could be carried out 120 min later. The suture was slowly and gradually withdrawn when the rats were maintained under anesthesia, so that the proximal end of the suture returned to the ECA, thereby initiating reperfusion of the middle cerebral artery. Animals were administered for a single dose immediately after reperfusion (within 10 min). 3 groups were established, namely a model control group, a compound (I) i.v. group (30 mg/kg), and a compound (I) p.o. group (60 mg/kg). Animals were euthanized 24 h after ischemia reperfusion, and the brains were rapidly taken, frozen, and dissected for TTC staining. The normal tissues were rose-red after staining, and the infarcted tissues were white. The infarct size (%) percentage, calculated as the weight of infarcted tissues to the weight of the whole brain, is used to evaluate the degree of cerebral ischemic injury in rats.

On the first day post-surgery, TTC staining analysis revealed that the cerebral infarct size in the model control group is 21.63±5.66%, and the cerebral infarct sizes of the compound (I) i.v. group and the compound (I) p.o. group are 13.61±3.66% and 14.88±5.11%, respectively. It shows that both the compound (I) i.v. group and the compound (I) p.o. group can significantly reduce the cerebral infarct size of animals (p=0.0025 and p=0.0389); meanwhile, the cerebral infarction inhibition rates of the animals in the compound (I) i.v. group and the compound (I) p.o. group are 37.1% and 31.2%, respectively. These results collectively demonstrate that the compound (I) can effectively ameliorate the outcome of cerebral infarction in rats, as detailed in Table 4.

TABLE 4

Cerebral infarct size and cerebral infarction inhibition rate of experimental animals

| Group | Infarct Size (%) | Cerebral infarction inhibition rate (%) |
|---|---|---|
| Model control group (N = 13) | 21.63 ± 5.66 | — |
| Compound (I) i.v. group (N = 12) | 13.61 ± 3.66** | 37.1 |
| Compound (I) p.o. group (N = 10) | 14.88 ± 5.11* | 31.2 |

Note:
the data in the table are all expressed as Mean ± standard deviation (Mean ± SD); "N" represents the number of animals in each group for statistical analysis; "—" represents no data for this item; *represents p < 0.05 compared with animals in themodel control group; **represents p < 0.01 compared with animals in the model control group.

Test 4: Middle and Long-Term Pharmacodynamic Study of Compound Herein in Rat Cerebral Stroke Model Middle cerebral artery occlusion (MCAO) models of SD rata were constructed by using the suture occlusion method. The rats were administered with the test compound for 28 consecutive days. The pharmacodynamic evaluation on the test compound for cerebral stroke was obtained based on general observation and neurobehavioral assessment.

After anesthesia induction with 3.0% isoflurane in SD rats (240-280 g), the operation was performed and the right common carotid artery (CCA), and the right-side neck area was dissected to reveal the right common carotid artery (CCA), external carotid artery (ECA) and internal carotid artery (ICA). The ECA was ligated. The ICA was temporarily occluded. Sutures were threaded at both the proximal end and the distal end of CCA. The distal end was securely ligated, and a loosely tied knot was placed at the proximal end. A small incision was made on the CCA between these two sutures. A No. 4-0 suture was inserted through the incision of CCA and slowly and gently pushed into the ICA. The threading was stopped temporarily when reaching the artery clamp of ICA. The pre-ligation suture was further tightened. The artery clamp blocking the blood flow in the ICA was removed, allowing the suture occlusion to be advanced into the ICA until it entered the intracranial region. When the suture was inserted about 18 mm away from the bifurcation of the CCA, slight resistance was felt, which shows the head end of the suture already entered the anterior cerebral artery (ACA), and the opening of the middle cerebral artery was already blocked by the side wall of the suture occlusion. The insertion was stopped at the moment, and the time was recorded. The artery clamp on the CCA was removed and the incision was closed after no active bleeding was observed. The ischemic rats were placed at room temperature to keep their body temperature at 37° C., and anesthesia induction could be carried out 120 min later. The suture was slowly and gradually withdrawn when the rats were maintained under anesthesia, so that the proximal end of the suture returned to the ECA, thereby initiating reperfusion of the middle cerebral artery. Animals received the designated dosage immediately (within 10 min) after reperfusion. This dosing regimen continued once daily for a duration of 28 days, with the day of operation being defined as D1 (Day 1). A total of 5 groups were set, sham surgery group, model control group, NBP group (60 mg/kg, p.o., q.d), compound (I) low dose p.o. group (6 mg/kg, p.o., q.d), and a compound (I) high dose p.o. group (20 mg/kg, p.o., q.d). During administration, all animals were subjected to grid walking tests (D7, D14, D21, and D28, 4 times in total) and novel object recognition tests (adaptation for novel object recognition on D26, test on D27). After the completion of the 28-day dosing period, all surviving animals in the study were euthanized, and their brains were rapidly collected for pathological analysis.

(1) The results of the grid walking tests showed that: one week after the operation, the misstep frequency of animals in the model control group is 7.24±3.59 times, and the misstep frequencies of the NBP group, the compound (I) low dose group, and the compound (I) high dose group are 7.37±3.03 times, 5.33±2.33 times, and 4.23±1.44 times, respectively, wherein the misstep frequency of animals in the compound (I) high dose group significantly reduced compared with that of animals in the model control group (p=0.0172); 2-3 weeks after the operation, the misstep frequency of animals in the model control group gradually reduced due to the gradual recovery of the motor function, and the misstep frequency of the compound (I) high dose group showed no statistically significant difference from that of the model control group but still demonstrated a reduced trend. 4 weeks after the modeling, the misstep frequency of animals in the model control group reduced to the level of animals in the sham surgery group. The above results demonstrate that the compound (I) exhibits efficacy in ameliorating walking dysfunction in animals after cerebral stroke (see Table 5 for details).

TABLE 5

Results of grid walking test

| Group | Misstep frequency (times) | | | |
|---|---|---|---|---|
| | 1 W | 2 W | 3 W | 4 W |
| Sham surgery group (12) | 0.96 ± 0.66 | 0.79 ± 0.56 | 0.88 ± 0.82 | 1.79 ± 0.92 |
| Model control group (N = 17) | 7.24 ± 3.59 | 5.35 ± 4.40 | 4.09 ± 3.140 | 1.59 ± 0.84 |
| NBP group (N = 15) | 7.37 ± 3.03 | 8.10 ± 2.97 | 6.27 ± 2.890 | 2.10 ± 1.46 |
| Compound (I) low dose group (N = 12) | 5.33 ± 2.33 | 6.33 ± 3.53 | 4.38 ± 2.44 | 2.58 ± 1.55 |
| Compound (I) high dose group (N = 13) | 4.23 ± 1.44* | 3.23 ± 2.56 | 2.50 ± 0.81 | 1.42 ± 1.11 |

Note:
the data in the table are all expressed as Mean ± standard deviation (Mean ± SD);
"N" represents the number of animals in each group for statistical analysis, "1 W, 2 W, 3 W, and 4 W" represents 1 week, 2 weeks, 3 weeks, and 4 weeks after the operation, respectively; *represents $p < 0.05$ compared with the model control group.

(2) A novel object recognition test was performed on the last day of the treatment and the novel object recognition index (NRI) of animals in each group was calculated. The NRI of animals in the model control group was 54.81±21.94%, which was not significantly different from the familiar object recognition index (FRI), and the NRI values of animals in the NBP group, the compound (I) low dose group, and the compound (I) high dose group were 70.97±22.57%, 70.98±22.60%, and 71.66±17.06%, respectively, wherein for the NBP group, the compound (I) low dose group, and the compound (I) high dose group, the NRI and FRI were significantly different (p=0.0074, p=0.0212, and p=0.0009, respectively), and the NRI values of the compound (I) low dose group and the compound (I) high dose group were comparable to animals in the sham surgery group (66.51±10.80%). The above results exhibit that the compound (I) can significantly ameliorate the cognitive disorder of animals after cerebral stroke (see Table 6 for details).

TABLE 6

Results of novel object recognition tests

| Group | Sniffing time (S) | | Recognition index (%) | |
|---|---|---|---|---|
| | Novel object | Familiar object | Novel object | Familiar object |
| Sham surgery group (11) | 10.52 ± 4.00 | 5.70 ± 3.19 | 66.51 ± 10.80*** | 33.49 ± 10.80 |
| Model control group (N =1 4) | 3.82 ± 3.40 | 2.70 ± 2.22 | 54.81 ± 21.94 | 45.19 ± 21.94 |
| NBP group (N = 13) | 4.94 ± 3.60 | 1.60 ± 1.01 | 70.97 ± 22.57** | 29.03 ± 22.57 |
| Compound (I) low dose group (N = 10) | 4.74 ± 3.61 | 1.54 ± 1.10 | 70.98 ± 22.60* | 29.02 ± 22.60 |
| Compound (I) high dose group (N = 13) | 5.62 ± 3.60 | 2.20 ± 1.66 | 71.66 ± 17.06** | 28.34 ± 17.06 |

Note:
the data in the table are all expressed as Mean ± standard deviation (Mean ± SD); "N" represents the number of animals in each group for statistical analysis; *represents $p < 0.05$ compared with the model control group, represents $p < 0.01$ compared with the model control group, and *represents $p < 0.001$ compared with the model control group.

(3) Pathological examination: 1) the restoration range: samples with a restoration area range of >30% are considered to be good in recovery, while samples with a restoration area range of ≤30% are considered to be poor in recovery. The proportion of animals in the model control group showing good recovery was 17.6%, the proportion of animals with restoration area >30% in the NBP group, the compound (I) low dose group, and the compound (I) high dose group were 21.4%, 33.3%, and 75.0%, respectively, and the compound (I) high dose group showed the best recovery condition and was significantly different from the model control group (Chi-square, p=0.0080); the above results show that the compound (I) has the effect of promoting the restoration of the infarction area (see Table 7 for details); 2) the number of perfused blood vessels in the infarction restoration area: the number of erythrocyte-containing blood vessels was compared using two criteria: ≤10 and >10 vessels. For all animals in the sham surgery group, the number of blood vessels in perfused state was greater than 10, and the proportion was 100%; in the model control group, the number of animals having ≤10 erythrocyte-containing blood vessels in the infarction restoration area and that of animals having >10 erythrocyte-containing blood vessels in the infarction restoration area were 10 and 7, respectively, and the proportion of animals having >10 erythrocyte-containing blood vessels was 41.2%; in the NBP treatment group, the number of animals having ≤10 erythrocyte-containing blood vessels in the infarction restoration area and that of animals having >10 erythrocyte-containing blood vessels in the infarction restoration area were 1 and 14, respectively, and the proportion of animals having >10 erythrocyte-containing blood vessels was 93.3%, which showed statistical significance compared with that of the model control group (Chi-square, p=0.0028); the number of animals having ≤10/>10 erythrocyte-containing blood vessels in the infarction restoration area of the compound (I) low dose group and that of the compound (I) high dose group were 0/12 and 1/12, respectively, and the number of animals having >10 erythrocyte-containing blood vessels was significantly greater than that of the model control group (Chi-square, p=0.0012, p=0.0076). In addition, for the compound (I) low dose group and the compound (I) high dose group, the proportion values of animal samples having >10 erythrocyte-containing blood vessels in the restoration area were 100% and 92.3%, respectively, both being no less than 90%. The above results show that the compound (I) can significantly improve the blood vessel perfusion degree of the cerebral infarction restoration area of animals with cerebral stroke after treatment for 28 consecutive days (see Table 8 for details).

TABLE 7

Summary for sample recovery in each group

| Group | Number of samples: Restoration area ≤30% | Number of samples: Restoration area >30% | Proportion of samples showing good recovery (%) |
|---|---|---|---|
| Sham surgery group (12) | — | 12 | 100 |
| Model control group (N = 17) | 14 | 3 | 17.6 |
| NBP group (N = 14) | 11 | 3 | 21.4 |
| Compound (I) low dose group (N = 12) | 8 | 4 | 33.3 |
| Compound (I) high dose group (N = 12) | 3 | 9** | 75.0 |

Note:
"N" represents the number of animals in each group for statistical analysis; **represents $p < 0.01$ compared with the model control group as determined by Chi-square.

TABLE 8

Summary for abundance of perfused blood vessels in each group

| Group | Number of erythrocyte-containing blood vessels: ≤10 | Number of erythrocyte-containing blood vessels: >10 | Proportion of samples having >10 erythrocyte-containing blood vessels (%) |
|---|---|---|---|
| Sham operation group (12) | — | 12 | 100 |
| Model control group (N = 17) | 10 | 7 | 41.2 |
| NBP group (N = 15) | 1 | 14** | 93.3 |
| Compound (I) low dose group (N = 12) | 0 | 12** | 100 |
| Compound (I) high dose group (N = 13) | 1 | 12** | 92.3 |

Note:
"N" represents the number of animals in each group for statistical analysis; **represents $p < 0.01$ compared with the model control group as determined by Chi-square.

The invention claimed is:

1. A compound of formula (II) or a pharmaceutically acceptable salt thereof:

(II)

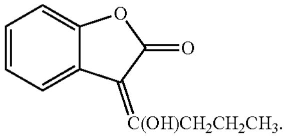

2. A compound of formula (I) or a pharmaceutically acceptable salt thereof:

(I)

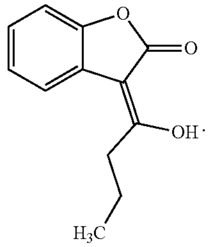

3. A single crystal of the compound of formula (I) or the pharmaceutically acceptable salt thereof according to claim 2, wherein the single crystal has the following unit cell parameters:

| Crystal system | Monoclinic |
|---|---|
| Space group | $P2_1/c$ |
| a/Å | 7.318 (6) |
| b/Å | 20.279 (17) |
| c/Å | 7.458 (7) |
| α/° | 90 |
| β/° | 111.417 (16) |
| γ/° | 90 |
| Unit cell volume/Å3 | 1030.2 (16) |
| Z | 4. |

4. A pharmaceutical composition, comprising the compound of formula (II) or the pharmaceutically acceptable salt thereof according to claim 1.

5. A method comprising administering an effective amount of a medicament for treating diseases related to cerebral ischemic injury selected from the group consisting of ischemic cerebral stroke, vascular dementia, post-ischemic inflammation, convulsion, ischemic neuronal injury and necrosis to a subject in need thereof, wherein the medicament comprises the compound of formula (II) or the pharmaceutically acceptable salt thereof according to claim 1.

6. A method for synthesizing a compound of (H) formula (I), wherein the compound of formula (I) is prepared as follows:

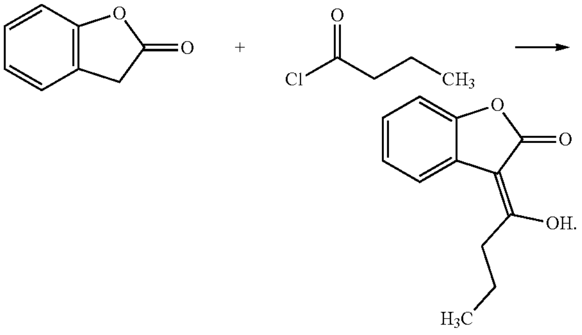

(I)

7. A method for preparing the single crystal according to claim 3, comprising dissolving the compound of formula (I) in petroleum ether, filtering, covering filtrate with a pinhole wrap, and placing the filtrate in a ventilated environment to allow a solvent to slowly evaporate at room temperature, thus obtaining the single crystal.

8. A pharmaceutical composition, comprising the compound of formula (I) or the pharmaceutically acceptable salt thereof according to claim 2.

9. A pharmaceutical composition, comprising the single crystal of the compound of formula (1) or the pharmaceutically acceptable salt thereof according to claim 3.

10. A method comprising administering an effective amount of a medicament for treating diseases related to cerebral ischemic injury selected from the group consisting of ischemic cerebral stroke, vascular dementia, post-ischemic inflammation, convulsion, ischemic neuronal injury and necrosis to a subject in need thereof, wherein the medicament comprises the compound of formula (I) or pharmaceutically acceptable salt thereof according to claim 2.

11. A method comprising administering an effective amount of a medicament for treating diseases related to cerebral ischemic injury selected from the group consisting of ischemic cerebral stroke, vascular dementia, post-ischemic inflammation, convulsion, ischemic neuronal injury and necrosis to a subject in need thereof, wherein the medicament comprises the single crystal according to claim 3.

12. A method comprising administering an effective amount of a medicament for treating diseases related to cerebral ischemic injury selected from the group consisting of ischemic cerebral stroke, vascular dementia, post-ischemic inflammation, convulsion, ischemic neuronal injury and necrosis to a subject in need thereof, wherein the medicament comprises the composition according to claim 4.

13. A method for preparing a single crystal comprising dissolving the compound of formula (I) according to claim 2 in petroleum ether solvent, filtering, covering filtrate with a pinhole wrap, and placing the filtrate in a ventilated environment to allow the solvent to slowly evaporate at room temperature, thus obtaining the single crystal.

* * * * *